US00PP22056P2

(12) United States Plant Patent
Danziger

(10) Patent No.: US PP22,056 P2
(45) Date of Patent: Aug. 2, 2011

(54) ***CALIBRACHOA* PLANT NAMED 'DANOA53'**

(50) Latin Name: ***Calibrachoa* sp.**
Varietal Denomination: DANOA53

(75) Inventor: Gavriel Danziger, Moshav Nir-Zvi (IL)

(73) Assignee: 'DAN' Danziger Flower Farm

( * ) Notice: Subject to any disclaimer, the term of this patent is extended or adjusted under 35 U.S.C. 154(b) by 0 days.

(21) Appl. No.: 12/661,257

(22) Filed: Mar. 12, 2010

(51) Int. Cl.
*A01H 5/00* (2006.01)

(52) U.S. Cl. ..... Plt./413

(58) Field of Classification Search ..... Plt./413
See application file for complete search history.

(56) References Cited

OTHER PUBLICATIONS

Print-out of application number and publication date from Community Plant Variety Office (CPVO) website for corresponding, CPVO application No. 2010/0389 filed Feb. 18, 2010 (1 page). (http://www.cpvoextranet.cpvo.europa.eu).

*Primary Examiner* — Annette H Para

(57) ABSTRACT

A new and distinct cultivar of *Calibrachoa* sp. plant named 'DANOA53' characterized by having flowers that are mainly white, with pink veins, measuring about 2 to 3 cm in size, measuring about 2 to 3 cm in size; mounded growth habit; medium floriferous flowering habit with a long blooming season; and suitable for patios and outdoors plant beddings.

2 Drawing Sheets

Latin name of the genus and species of the plant claimed: *Calibrachoa* sp.

Variety denomination: 'DANOA53'.

BACKGROUND OF THE INVENTION

The present invention relates to a new and distinct cultivar of *Calibrachoa* plant, botanically known as *Calibrachoa* sp., and hereinafter referred to by the cultivar name 'DANOA53'.

Background Description of the Genus *Calibrachoa*

The genus *Petunia* was originally established in 1803 by A.L. Jussieu, who described both P. *parviflora* and P. *nyctaginiflora* as type species. Using a non-horticultural system that selected the first mentioned species as the type species (lectotype), N.L. Britton and H.A. Brown declared P. *parviflora* as the type species for *Petunia* in 1913.

During the 1980's and 1990's, H.J. Wijsman published a series of articles regarding the ancestry of P. *hybrida*, the Garden *Petunia*, and the inter-relationship of several species classified as *Petunia*. These studies discovered that P. *hybrida* and its ancestral species, P. *nyctaginiflora* (=P. *axillaris*) and P. *violacea* (=P. *integrifolia*), possessed 14 pairs of chromosomes while several other species, including P. *parviflora*, possessed 18 pairs of chromosomes. Since P. *parviflora* was the lectotype species for the *Petunia* genus, Wijsman and J.H. de Jong proposed transferring the 14 chromosome species to the genus *Stimoryne*. Horticulturists opposed reclassifying the Garden *Petunia* and in 1986, Wijsman proposed the alternative of making P. *nyctaginiflora* the lecototype species for Petunia and transferring the 18 chromosome species to another genus. The I.N.G. Committee adopted this proposal. By 1990 Wijsman had transferred several species, including P. *parviflora* (=C. *parviflora*) to *Calibrachoa*, originally established by Llave and Lexarza in 1825. *Calibrachoa parviflora* (=C. *mexicana* Llave & Lexarza) is now the type species for the genus *Calibrachoa*.

Classification of the current *Petunia* and *Calibrachoa* species is still in progress. New species are also being identified. Consequently a proper description has not been written for the *Calibrachoa* genus. *Calibrachoa* can, however, be distinguished from *Petunia* based on the higher chromosome number, chromosome morphology, plant branching habit and type of flower bud aestivation. Whereas *Petunia* species bear a flower peduncle and one new stem from a node, *Calibrachoa* bear a flower peduncle and three stems. *Petunia* species have a cochlear corolla bud, and a single outermost petal covers the other four, radially folded and terminally contorted petals. *Calibrachoa* flower buds are flat with all five petals linearly folded and the two lower petals forming a cover around the three other petals and fused together.

Breeding and Selection of New Cultivar

The new *Calibrachoa* cultivar is a product of a planned breeding program conducted by the Inventor, Gavriel Danziger, in Moshav Mishmar Hashiva, Israel. The objective of the breeding program was to develop a new *Calibrachoa* cultivar having attractive flower colors, a desirable plant habit, and a strong, vigorous growth habit.

The new *Calibrachoa* 'DANOA53' originated from a cross made in a controlled breeding program by the inventor in 2006 in Moshav Mishmar Hashiva, Israel. The female or seed parent is the *Calibrachoa* designated 'CA-1508' (unpatented) and the male or pollen parent is the *Calibrachoa* designated 'CA-1006' (unpatented). The new *Calibrachoa* 'DANOA53' was discovered and selected by the inventor as a single flowering plant within the progeny of the stated cross in a controlled environment in March of 2008 in Moshav Mishmar Hashiva, Israel.

Asexual reproduction of the new *Calibrachoa* 'DANOA53' by vegetative cuttings was first performed in April of 2008 in Moshav Mishmar Hashiva, Israel, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'DANOA53' which in combination distinguish this *Calibrachoa* as a new and distinct cultivar:

1. Flowers that are mainly white, with pink veins, measuring about 2 to 3 cm in size;
2. Mounded growth habit;
3. Medium floriferous flowering habit with a long blooming season; and
4. Suitable for patios and outdoors plant beddings.

Plants of the new *Calibrachoa* 'DANOA53' differ from plants of the parents, *Calibrachoa* 'CA-1508' (unpatented) and *Calibrachoa* 'CA-1006' (unpatented), in the characteristics described in Table 1.

TABLE 1

| Characteristic | New Cultivar 'DANOA53' | Female Parent 'CA-1508' (unpatented) | Male Parent 'CA-1006' (unpatented) |
|---|---|---|---|
| Branching Rate | Medium | Low | Medium |
| Flower Color | White, RHS 155D, with pink veins, closest to red-purple, RHS 73A | Red-purple, RHS N74C | White, RHS N999D (mini color chart) |
| Flower Diameter | About 2 to 3 cm | About 2.5 cm | About 2.5 cm |

Of the many commercial cultivars known to the present inventor, the most similar in comparison to the new *Calibrachoa* 'DANOA53' is *Calibrachoa* sp. 'DANOA36' (patented, U.S. Plant Pat. No. 19,459), in the characteristics described in Table 2:

| Characteristic | New Cultivar 'DANOA49' | Comparison Cultivar 'DANOA36' (patented, U.S. Plant Pat. No. 19,459) |
|---|---|---|
| Branching Rate | Medium | High |
| Flower Color | White, RHS 155D, with pink veins, closest to red-purple, RHS 73A | Yellow-orange, RHS 16C, with red halo |
| Flower Diameter | About 2 to 3 cm | About 2 to 2.5 cm |

BRIEF DESCRIPTION OF THE PHOTOGRAPHS

The accompanying photographs illustrate the overall appearance of the new *Calibrachoa* cultivar 'DANOA53' showing the colors as true as is reasonably possible with colored reproductions of this type. Colors in the photographs may differ slightly from the color value cited in the detailed botanical description, which accurately describe the color of 'DANOA53'.

DETAILED BOTANICAL DESCRIPTION

Figure 1:
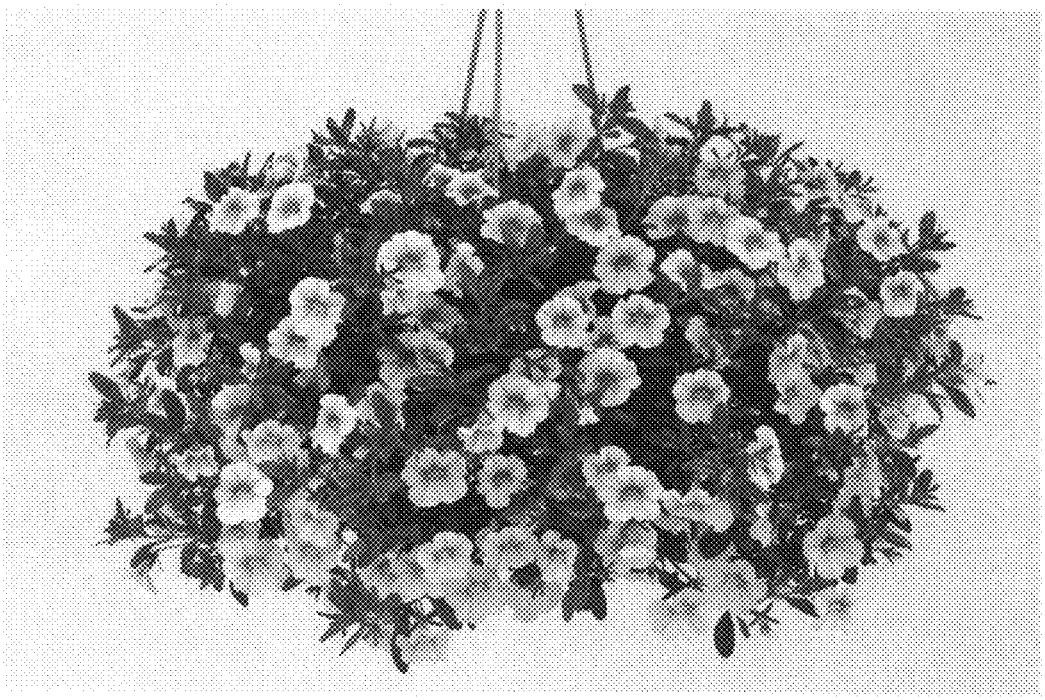
FIG. 1 shows a side view perspective a typical flowering plant of 'DANOA53' in a hanging planter, at 2 months of age.
Figure 2:
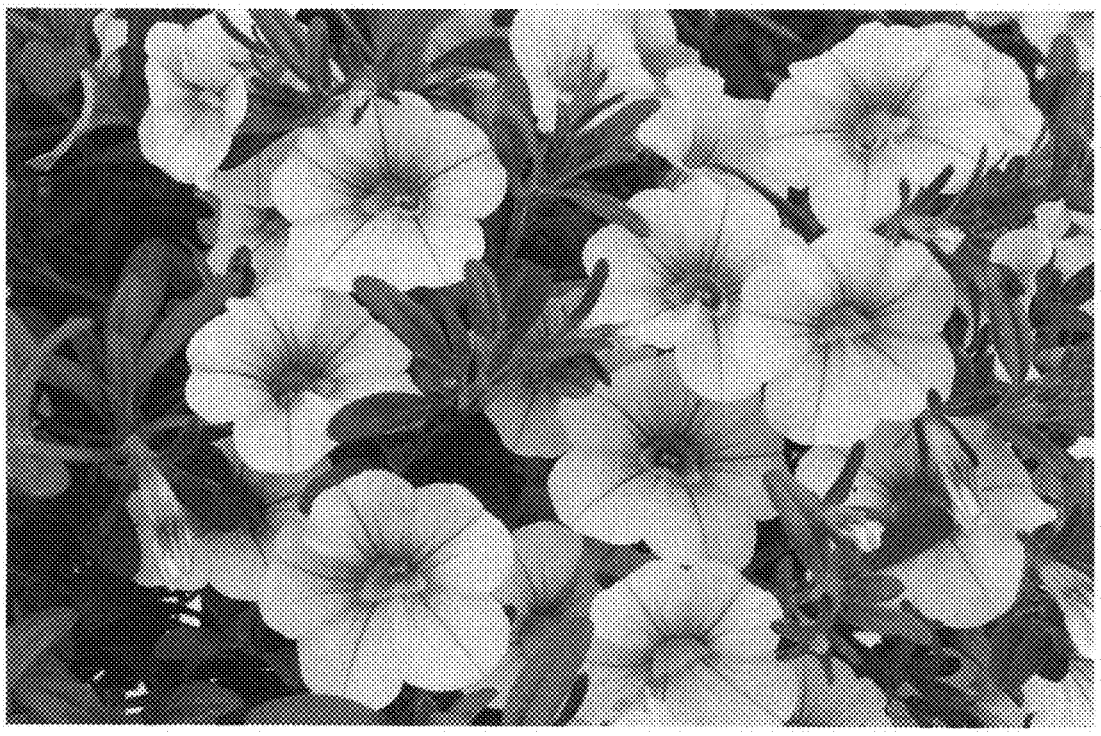
FIG. 2 shows a close-up view of the typical flowers and leaves of 'DANOA53', at 2months of age.

The new *Calibrachoa* 'DANOA53' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of the new cultivar 'DANOA53' as grown in a greenhouse in Moshav Mishmar Hashiva, Israel, under conditions which closely approximate those generally used in commercial practice.

Plants of 'DANOA53' are grown outdoors in moderate climate and grown indoors during the winter. Irrigation and fertilization are needed on a regular basis. For optimal growth, grow plants of 'DANOA53' in full sunlight. Plants of 'DANOA53' are fully grown plant in 3 months when grown in full sunlight, and bloom all year-round in a moderate climate. 'DANOA53' is used as suitable for patios and outdoors plant beddings.

Color references are made to the Royal Horticultural Society Colour Chart (R.H.S.), 2001 edition, except where general colors of ordinary significance are used. Color values were taken under daylight conditions at approximately 12:00 noon in Moshav Mishmar Hashiva, Israel. The age of the plant described is 2 months.

Classification:
- *Botanical.*—*Calibrachoa* sp.
- *Commercial name.*—Noa Almond Blossom.

Parentage:
- *Female or seed parent.*—*Calibrachoa* sp. designated 'CA-1508' (unpatented).
- *Male or pollen parent.*—*Calibrachoa* sp. designated 'CA-1006' (unpatented).

Optimal growth conditions:
- *Light intensities.*—Full sunlight.
- *Temperature.*—Day: 20° C. to 35° C. Night: 17° C. to 23° C.
- *Fertilization.*—A balanced fertilizer with level of 200 ppm Nitrogen.
- *Growth regulators.*—None.

Propagation:
- *Type.*—Cutting of side shoots.
- *Rooting habit and description.*—Easy to root; root from cutting base.
- *Time to initiate roots.*—About 7 to 10 days at 25° C.
- *Time to produce a rooted cutting.*—About 16 days at 25° C.

Plant:
- *General appearance and form.*—Height: About 25 cm. Spread: About 50 cm.
- *Growth rate and habit.*—Compact.
- *Branching habit and description.*—Medium branching rate.

Lateral branches:
- *Quantity per plant.*—About 15 to 20.
- *Length.*—About 15 cm.
- *Diameter.*—About 0.2 cm.
- *Texture.*—Pubescent.
- *Color.*—Green, RHS 139A.
- *Internode length.*—About 2 cm.
- *Internode color.*—Green, RHS 139A.
- *Average number of flowers per lateral branch.*—About 6.

Foliage:
- *Arrangement.*—Opposite.
- *Overall shape of leaf.*—Oval.
- *Apex.*—Rounded.

*Base.*—Acute.
*Length.*—About 2 cm.
*Width.*—About 1 cm.
*Margin.*—Entire.
*Texture.*—Upper: Pubescent. Under: Pubescent.
*Color of upper surface.*—Mature leaf: Green, RHS 139A. Immature leaf: Green, RHS 139A.
*Color of under surface.*—Mature leaf: Green, RHS 139A. Immature leaf: Green, RHS 139A.
*Venation.*—Pattern: Pinnate. Color: Upper surface: Green, RHS 139A. Under surface: Green, RHS 139A.
*Petiole.*—None.

Inflorescence:
*Flower type and habit.*—Single, horizontal facing salverform flowers. Flowers persistent and not fragrant.
*Flowering season.*—All year round in moderate climate.
*Flowering response.*—Fully grown plant in 3 months.
*Winter hardiness.*—Frost tender. Temperature below 5° C. may damage plants.
*Lastingness of the individual bloom.*—About 3 to 6 days.
*Fragrance.*—None.
*Bud.*—Rate of opening: About 1 to 3 days, according to weather. Length: The young bud is about 1 cm, and it lengthens to about 1.5 cm before opening. Diameter: About 0.5 cm. Shape: Tubular. Immature Color: Green-yellow, RHS 1C. Mature Color: Green-yellow, RHS 1C.
*Corolla.*—Arrangement and appearance: Five petals, fused into flared trumpet.
*Flower size.*—Flower Depth: About 1.5 cm. Flower Diameter: About 3.0 cm. Flower Tube Length: About 1.0 cm. Flower Tube Diameter: About 1.0 cm.
*Petals.*—Petal Number: 5. Petal size: Length: About 0.8 cm to 1.3 cm. Width: About 1.5 cm to 1.8 cm. Petal Shape: Overall: Obcordate. Apex shape: Blunt. Base shape: Fused. Margin: Entire. Texture: Smooth. Petal Color: When opening: Upper surface: White, RHS 155D, with pink veins, closest to red-purple, RHS 73A. Under surface: White, RHS 155D, with pink veins, closest to red-purple, RHS 73A. When fully opened: Upper surface: White, RHS 155D, with pink veins, closest to red-purple, RHS 73A. Under surface: White, RHS 155D, with pink veins, closest to red-purple, RHS 73A. Flower throat color (inside): Yellow, RHS 2A. Flower tube color (outside): Green-yellow, RHS 1B.
*Sepals.*—Arrangement and appearance: Single whorl of five sepals, fused at base. Sepal Number: 5. Sepal size: Length: About 1.5 cm. Width: About 0.3 cm. Sepal Shape: Overall: Elliptic. Apex shape: Truncate. Base shape: Fused. Margin: Entire. Texture: Lustrous. Sepal Color: Upper surface Green, RHS 143A. Under surface: Green, RHS 143B.
*Peduncles.*—Length: About 2.5 cm. Width: About 0.1 cm. Angle: About 45° from stem axis. Strength: Flexible. Texture: Smooth. Color: Green, RHS 143B.

Reproductive organs:
*Androecium.*—Stamen: Number: 5. Color: Yellow, RHS 2A. Anther: Shape: Round. Length: About 0.1 mm. Color: Yellow, RHS 2A. Filaments: Length: About 0.6 mm. Color: Yellow, RHS 2A. Pollen: Amount: Plenty. Color: Yellow, RHS 2A.
*Gynoecium.*—Pistils: Quantity: 1. Length: About 0.7 mm. Stigma: Shape: Round. Width: About 0.1 mm. Color: Green, RHS 143A. Style: Length: About 0.7 mm. Color: Green, RHS 143A. Ovary: Position: Superior. Length: About 0.2 mm. Width: About 0.1 mm. Color: Green, RHS 143A.

Seeds:
*Quantity.*—About 5 to 10.
*Length.*—About 0.1 mm.
*Width.*—About 0.1 mm.
*Shape.*—Round.
*Texture.*—Smooth.
*Color.*—Black, RHS 202A.

Fruit:
*Quantity.*—Few, when naturally pollinated.
*Type.*—Capsule.
*Length.*—About 0.4 mm.
*Width.*—About 0.3 mm.
*Shape.*—Ovoid.
*Texture.*—Smooth.
*Color.*—Green, RHS 139A.

Disease/pest resistance: No information is currently available.

Disease/pest susceptibility: No information is currently available.

Low temperature tolerance: Sensitive to temperatures below 4° C.

What is claimed is:

1. A new and distinct cultivar of *Calibrachoa* sp. plant named 'DANOA53', substantially as illustrated and described herein.

* * * * *